(12) United States Patent
Mao et al.

(10) Patent No.: US 10,982,295 B2
(45) Date of Patent: Apr. 20, 2021

(54) **STAIN *SACCHAROMYCES CEREVISIAE* M 2016785 PRODUCING HIGH CONCENTRATION OF β-PHENYLETHANOL AND APPLICATION THEREOF**

(71) Applicant: Jiangnan University, Wuxi (CN)

(72) Inventors: Jian Mao, Wuxi (CN); Shuang ping Liu, Wuxi (CN); Zhongwei Ji, Wuxi (CN); Xiao Han, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 129 days.

(21) Appl. No.: 16/226,622

(22) Filed: Dec. 19, 2018

(65) Prior Publication Data
US 2019/0119764 A1    Apr. 25, 2019

Related U.S. Application Data

(63) Continuation of application No. PCT/CN2017/100446, filed on Sep. 5, 2017.

(30) Foreign Application Priority Data

May 25, 2017 (CN) .................. 201710378178.3
May 25, 2017 (CN) .................. 201710379232.6

(51) Int. Cl.
*A23L 27/50* (2016.01)
*C12J 1/04* (2006.01)
(Continued)

(52) U.S. Cl.
CPC .............. *C12R 1/865* (2013.01); *A23L 27/00* (2016.08); *A23L 27/50* (2016.08); *C12G 1/0203* (2013.01);
(Continued)

(58) Field of Classification Search
None
See application file for complete search history.

(56) References Cited

U.S. PATENT DOCUMENTS

3,552,981 A * 1/1971 Luksas .................. A23C 21/02
426/41

FOREIGN PATENT DOCUMENTS

CN    101701195 B * 10/2012
CN    102816708 A * 12/2012
(Continued)

OTHER PUBLICATIONS

Li, Yudong; et al; "Genomic Evolution of *Saccharomyces cerevisiae* under Chinese Rice Wine Fermentation" Genome Biology Evolution, 6, 2516-2526, 2014 (Year: 2014).*
(Continued)

*Primary Examiner* — David W Berke-Schlessel
(74) *Attorney, Agent, or Firm* — IPro, PLLC

(57) ABSTRACT

The present invention discloses a strain *S. cerevisiae* M 2016785 producing high concentration of β-phenylethanol and application thereof, and belongs to the technical field of industrial microorganisms. The strain *S. cerevisiae* M 2016785 producing high concentration of β-phenylethanol according to the present invention was deposited in China Center for Type Culture Collection (CCTCC) on Dec. 26, 2016 with the accession number OF CCTCC NO: M 2016785. The strain of the present invention has the high β-phenylethanol production capacity, and is applied in the fermentation of Huangjiu, the fermentation of cooking wine,
(Continued)

the brewing of vinegar, the fermentation of soybean sauce and the fermentation of Baijiu, in which the content of β-phenylethanol can reach 410 mg/L, 450 mg/L, 300 mg/L, 200 mg/L, 110 mg/L and 370 mg/L respectively, and effectively increases the concentration of the flavor substance such as 2-phenylethyl acetate. The yeast strain of the present invention has good fermentation performance, obviously improves the β-phenylethanol content in the fermented product, and improves the quality of the fermented product, and thus has broad application prospects.

14 Claims, 4 Drawing Sheets

(51) Int. Cl.
| | |
|---|---|
| C12G 3/022 | (2019.01) |
| C12G 3/025 | (2019.01) |
| C12R 1/865 | (2006.01) |
| C12N 1/18 | (2006.01) |
| C12J 1/02 | (2006.01) |
| A23L 27/00 | (2016.01) |
| C12G 1/022 | (2006.01) |
| C12G 3/024 | (2019.01) |

(52) U.S. Cl.
CPC ............. *C12G 3/022* (2019.02); *C12G 3/024* (2019.02); *C12G 3/025* (2013.01); *C12J 1/02* (2013.01); *C12J 1/04* (2013.01); *C12N 1/18* (2013.01); C12G 2200/05 (2013.01)

(56) References Cited

FOREIGN PATENT DOCUMENTS

| CN | 102816708 A | 12/2012 |
|---|---|---|
| CN | 105861348 A | 8/2016 |
| KR | 20140079199 A | 6/2014 |
| WO | 2009098342 A1 | 8/2009 |

OTHER PUBLICATIONS

Solieri, Lisa; Giudici, Paolo; Vinegars of the World, Springer, New York, 2009 (Year: 2009).*

Yin, SHeng; et al; "Improving 2-Phenylethanol Production via Ehrlich Pathway Using Genetic Engineered *Saccharomyces cerevisiae* Strains" Current Microbiology, 70, 762-767, 2015 (Year: 2015).*

Cui Zhifeng, et al., Breeding of yeast strain with high yield of 2-phenylethanol. Journal of Zhejiang University of technology, 2008 (04): p. 427-430.

Huang Xiaoping, et al., Screening and identification of a yeast strain with high yield of 2-phenylethanol. Acta food and biotechnology, 2016.35 (05): p. 531-536.

Mei Jianfeng, et al., Mutation breeding of 2-phenylethanol by biotransformation. Food and fermentation industry, 2007 (05): p. 22-24.

Rong Shaofeng, Study on the production of β-phenylethanol by *Saccharomyces cerevisiae* as 2.1182. Food and fermentation industry, 2009.35 (08): p. 69-73.

Ye Mengqi. Study on the regulation of aroma compounds and FT-NIRS analysis method in cider brewing process [D]. Northwest agricultural and Forestry University, 2015.

* cited by examiner

STAIN *SACCHAROMYCES CEREVISIAE* M 2016785 PRODUCING HIGH CONCENTRATION OF β-PHENYLETHANOL AND APPLICATION THEREOF

TECHNICAL FIELD

The present invention relates to a strain *S. cerevisiae* producing high concentration of β-phenylethanol and application thereof, and belongs to the technical field of industrial microorganisms.

BACKGROUND

β-phenylethanol is an aromatic alcohol with a rose flavor, which is naturally found in plant essential oil such as jasmine and rose. It is also an important flavor and fragrance ingredient, and is widely used in cosmetics, tobacco and daily chemical products. As a special flavor substance in the fermented foods, β-phenylethanol can improve the flavor and overall quality of the fermented product. However, at present, some by-products which are difficult to remove will be produced during the chemical synthesis of β-phenylethanol, which may cause cancer risk and seriously affect product quality. Although an innocuous, harmless and superior-quality β-phenylethanol for food or other product production can be obtained via the physical extraction from natural plants, such extraction has a long production cycle, low yield, and high price, which is difficult to meet market demand.

β-phenylethanol in the fermented foods can be produced by microbial metabolism, the content of β-phenylethanol in the fermented foods can be improved by microbial fermentation, and the obtained product belongs to natural food. *S. cerevisiae* produces β-phenylethanol through the Ehrlich pathway and other metabolic pathways during fermentation. The β-phenylethanol content in fermented foods such as Huangjiu (Chinese rice wine) can reach about 100 mg/L. Although the concentration is already high, further increase of β-phenylethanol content is significant for enhancing the flavor of Huangjiu. Although the content of β-phenylethanol in wine can reach about 60 mg/L, it is necessary to further increase the β-phenylethanol content for the development of the characteristics of rose aromatic wine. Therefore, it is necessary to screen yeast with excellent performance.

Although the exogenous addition of precursor compounds such as L-phenylalanine can promote β-phenylethanol production by *S. cerevisiae* to increase β-phenylethanol content in fermented foods, the cost is relatively high and the original production formula of the food is changed. In addition, without exogenous addition of L-phenylalanine, a small number of non-*S. cerevisiae* yeasts such as *Pichia kudriavzevii* and *Marx Kluyveromyces* can produce a certain concentration of β-phenylethanol for increasing the concentration of β-phenylethanol in fermented foods. However, since non-*S. cerevisiae* has low ethanol production capacity, it cannot be used as a main strain for the fermentation of fermented foods such as alcohol and vinegar. Rafael et al. (Overproduction of 2-phenylethanol by industrial yeasts to improve organoleptic properties of bakers' products, International Journal of Food Microbiology, 2014, 180(1):7-12) reported application of baker's yeast strain producing high concentration of β-phenylethanol in baked goods that do not require to produce a high concentration of alcohol, but did not report on the alcohol-producing properties of the reported yeast. Although there have been reports on the application of several *S. cerevisiae* strains producing a certain concentration of alcohol for brewing foods, it is unclear whether the strains have a high alcohol production capacity or not. Since the stress ability of β-phenylethanol on yeast is significantly higher than that of ethanol, the ethanol production capacity of *S. cerevisiae* producing high concentration of β-phenylethanol is usually reduced, so the alcohol production capacity of *S. cerevisiae* producing high concentration of β-phenylethanol is low. Therefore, without exogenous addition of precursor compounds, *S. cerevisiae* producing high concentration of β-phenylethanol and ethanol has higher application value in the brewing industry.

SUMMARY

In order to solve the above problems, the present invention provides a strain *S. cerevisiae* M 2016785 which has high β-phenylethanol producing property and has excellent alcohol producing property without adding exogenous amino acids, and the application of the strain in Huangjiu, cooking wine, brewing vinegar, soybean sauce, Baijiu (Chinese liquor) and fruit wine. The strain has high β-phenylethanol production capacity and high flavor substance 2-phenylethyl acetate production capacity, and has good fermentation performance, can obviously increase the β-phenylethanol content in the fermented product, improve the quality of the fermented product, and has wide application prospects.

The first objective of the present invention is to provide a strain *S. cerevisiae* M 2016785 producing high concentration of β-phenylethanol, which was deposited in China Center for Type Culture Collection (CCTCC), Wuhan University, Wuhan, China on Dec. 26, 2016 with the accession number of CCTCC NO: M 2016785.

The strain *S. cerevisiae* M 2016785 of the present invention is a *S. cerevisiae* producing high concentration of β-phenylethanol which is obtained by using the *S. cerevisiae* screened from the fermenting mash of Huangjiu as a starting strain, upon ultraviolet mutagenesis, subjecting the resulted strain to the p-fluorophenylalanine resistance screening, then screening a strain with good growth vigour, inoculating it in the YPD liquid medium with 10% ethanol, subjecting it to the alcohol tolerance screening and the Huangjiu simulated liquid fermentation screening to obtain a strain with a relatively high β-phenylethanol yield, using it as the starting strain for normal temperature isobaric plasma mutagenesis, upon the second mutagenesis, subjecting the resulted strain to the p-fluorophenylalanine resistance screening and the fermentation characteristic screening.

The *S. cerevisiae* M 2016785 of the present invention has the following characteristics:

(1) when being applied to a Huangjiu fermentation system, Huangjiu obtained by fermentation has β-phenylethanol content up to 410 mg/L, 2-phenylethyl acetate content of 56 μg/L, and the alcohol content of 17% (v/v);

(2) when being applied to a cooking wine fermentation system, cooking wine obtained by fermentation has β-phenylethanol content up to 450 mg/L, 2-phenylethyl acetate content of 50 μg/L, and the alcohol content of 15% (v/v);

(3) when being applied to a brewing vinegar fermentation, in which the *S. cerevisiae* M 2016785 of the present invention is used instead of the seeding yeast, the obtained mash is then fermented by acetic acid, and the brewed vinegar has β-phenylethanol content of 300 mg/L and 2-phenylethyl acetate content of 45 μg/L;

(4) when being applied to the soybean sauce, in which the *S. cerevisiae* M 2016785 is inoculated into a soybean sauce fermentation system, soybean sauce obtained by fermentation has β-phenylethanol content of 200 mg/L;

(5) when being applied to the Baijiu, in which the *S. cerevisiae* M 2016785 is inoculated into a Baijiu fermentation system, distilled liquor has β-phenylethanol content of 110 mg/L, 2-phenylethyl acetate content of 64 μg/L, and alcohol content up to 65% (v/v);

(6) when being applied to a fermentation system of fruit wine (mulberry wine, hawthorn wine, bayberry wine, and *Aronia* wine), fruit wine obtained by pure fermentation has β-phenylethanol content up to 350 mg/L, 2-phenylethyl acetate content of 50 μg/L, and alcohol content of 14.5% (v/v);

(7) the colonies are white, round or elliptical with neat edges.

The second objective of the present invention is to provide a microbial agent containing the strain *S. cerevisiae* M 2016785:

In one embodiment of the present invention, the microbial agent contains live cells of strain *S. cerevisiae* M 2016785, freeze-dried strain *S. cerevisiae* M 2016785, immobilized cells of strain *S. cerevisiae* M 2016785, liquid microbial agent of strain *S. cerevisiae* M 2016785, solid microbial agent of strain *S. cerevisiae* M 2016785, or any other form of strain *S. cerevisiae* M 2016785.

The third objective of the present invention is to provide application of the strain *S. cerevisiae* M 2016785 or the microbial agent.

In one embodiment, the application refers to the application in the manufacture of fermented foods.

In one embodiment, the application refers to the application in the field of brewing technology.

The fourth objective of the present invention is to provide a fermented food obtained by taking the *S. cerevisiae* M 2016785 as a starter culture or a main starter culture.

In one embodiment, the fermented food is a brewed food.

In one embodiment, the brewed food is alcohol, vinegar or soybean sauce. The alcohol includes, but is not limited to, Huangjiu, cooking wine, Baijiu, and the like.

In one embodiment, the brewed food is Huangjiu, and the *S. cerevisiae* M 2016785 is used as a seeding yeast.

In one embodiment, the Huangjiu is brewed by adding the *S. cerevisiae* M 2016785 as a seeding yeast to the cooked or gelatinized raw material in an amount of 5% to 10%, and fermenting, pressing, sterilizing, aging, filtering, sterilizing and filling to obtain the Huangjiu.

In particular, in one embodiment, the Huangjiu is brewed by preparing the seeding yeast through culturing the *S. cerevisiae* M 2016785, then adding 4% of wheat qu(wheat koji) by total volume, adding 10% of seeding yeast by total volume to glutinous rice which has been gelatinized at high temperature, stirring well, then fermenting, pressing, sterilizing, aging, filtering, sterilizing and filling to obtain the Huangjiu.

In one embodiment, the brewed food is cooking wine.

In one embodiment, the cooking wine is brewed by firstly using the *S. cerevisiae* M 2016785 as a seeding yeast to obtain the Huangjiu, and then using the obtained Huangjiu to prepare the cooking wine.

In one embodiment, the brewed food is vinegar.

In one embodiment, the vinegar is brewed by firstly using the *S. cerevisiae* M 2016785 as a seeding yeast to obtain the Huangjiu, and then using the obtained Huangjiu as a raw material for acetic fermentation to brew the vinegar.

In one embodiment, the vinegar is brewed by solid-state fermentation or liquid-state fermentation.

In one embodiment, the brewed food is soybean sauce.

In one embodiment, the soybean sauce is brewed by using high-salt dilute-state fermentation or low-salt solid-state fermentation to prepare the soybean sauce.

In particular, in one embodiment, the high-salt dilute-state fermentation preparation of the soybean sauce is: mixing and steaming soybean meal and wheat, inoculating *Aspergillus oryzae*, adding salt water to make a soybean sauce mash have the salt content of 18% and the water content of 65%, stirring and mixing well; then inoculating the cultured *S. cerevisiae* M 2016785 into part of the steamed and cooled soybean meal and wheat, adding fresh water, and culturing to produce a seeding yeast M 2016785 to be added to a soybean sauce mash; inoculating the seeding yeast M 2016785 when the temperature of the soybean sauce mash is increased to 20° C. during the fermentation process; fermenting for 5 months; after the fermentation, pressing, filtering, and clarifying the soybean sauce mash to obtain the soybean sauce.

In particular, in one embodiment, the low-salt solid-state fermentation preparation of the soybean sauce is: mixing and steaming soybean meal and wheat, inoculating *A. oryzae*, adding salt water to make a soybean sauce mash have the salt content of 7% and the water content of 40%, stirring and mixing well; then inoculating the cultured *S. cerevisiae* M 2016785 into part of the steamed and cooled soybean meal and wheat, adding fresh water, and culturing to produce a seeding yeast M 2016785, inoculating the seeding yeast M 2016785 into the soybean sauce mash fermentation system, controlling the product temperature at 40° C.; fermenting for 15 d; after the fermentation, removing impurities and precipitates from the soybean sauce mash, and filtering and clarifying the resulted soybean sauce mash to obtain the soybean sauce.

In one embodiment, the brewed food is Baijiu.

In one embodiment, the Baijiu is brewed by additionally adding the *S. cerevisiae* M 2016785 when the Baijiu is fermented in a fermenting vat.

In one embodiment, the additional additive amount of *S. cerevisiae* M 2016785 in the brewing of the Baijiu is 1%.

The fifth objective of the present invention is to provide a method for enhancing the aroma of fruit wine, especially a method for enhancing the rose aroma of fruit wine, by using the *S. cerevisiae* M 2016785 of the present invention as a fermentation strain.

In one embodiment, the *S. cerevisiae* M 2016785 is lyophilized powder of the strain M 2016785.

In one embodiment, the method comprises adding the freeze-dried strain *S. cerevisiae* M 2016785 to the juice in an additive amount of 2%.

In one embodiment, the fruit wine is obtained by mixing and fermenting one or more of mulberry juice, hawthorn wine, bayberry juice and *Aronia* juice at a certain ratio.

In one embodiment, the fruit wine is mulberry wine, hawthorn wine, bayberry wine, *Aronia* wine, and the like.

In one embodiment, the method includes the following steps:

(1) cleaning fruit raw materials, crushing, pressing, and separating to obtain a juice;

(2) additionally adding white granulated sugar and stirring well;

(3) feeding 160 mg/L of potassium pyrosulfite, 100 mg/L of pectinase into a tank and stirring well;

(4) activating a seed solution of *S. cerevisiae* M 2016785, culturing in a YPD medium (1% yeast extract, 2% peptone, 2% glucose) for 12 h or longer; or taking 2% lyophilized powder of *S. cerevisiae* M 2016785 and stirring for 30-60 min at 38° C. to allow the dried strain to fully absorb water to obtain a bacterial solution;

(5) inoculating the activated seed solution or bacterial solution of lyophilized powder in the previous step into the fermentation tank for pre-fermentation; after inoculation, controlling the temperature at 23-25° C., starting the fermentation after 12-24 h, and controlling the temperature at 20-23° C. after starting the fermentation;

(6) determining whether it is necessary to supplement white granulated sugar and supplement amount according to the fermentation situation during the fermentation process; wherein the pre-fermentation time is 8-12 d;

(7) after the pre-fermentation, separating the yeast in the fermentation broth, and adding a certain concentration of sulfur dioxide to the fermentation broth for post-fermentation;

(8) controlling the post-fermentation temperature to be below 20° C., adding a clarifying agent, fully mixing, and fermenting for 16-24 d; and (9) filtering through draining the liquor at the bottom of the fermentation tank and filtering the upper liquid.

Advantages and Effects of the Present Invention (1) The present invention obtains a strain *S. cerevisiae* M 2016785 which has high β-phenylethanol producing property and excellent alcohol producing property without adding exogenous amino acids.

(2) The strain *S. cerevisiae* M 2016785 of the present invention can be used for the brewing of Huangjiu, cooking wine, vinegar, soybean sauce and Baijiu; when being used in the brewing of these products, not only high concentration of β-phenylethanol and high alcohol production capacity can be obtained, but also the content of other flavor ingredients or beneficial ingredients can be increased effectively, such as the content of 2-phenylethyl acetate.

(3) When the *S. cerevisiae* M 2016785 is used for preparing fruit wine, the content of β-phenylethanol in the finished fruit wine reaches 350 mg/L, which is increased by about 571% than that of the fruit wine brewed with a common yeast strain, the aroma of the fruit wine is significantly enhanced and a good alcohol production property is obtained, in which the alcohol content can reach 14.5% (v/v).

Biomaterial Preservation

A strain *S. cerevisiae* M 2016785 having a taxon name of *S. cerevisiae* BYC3 was deposited in China Center for Type Culture Collection, Wuhan University, Wuhan, China on Dec. 26, 2016 with the accession number of CCTCC NO: M 2016785.

DETAILED DESCRIPTION

The following is a detailed description of the present invention.

Example 1: Ultraviolet Mutagenesis and Screening

YPD liquid medium: 10 g/L of yeast extract, 20 g/L of peptone, fish powder, and 20 g/L of glucose.

YPD solid medium: 10 g/L of yeast extract, 20 g/L of peptone, fish powder, 20 g/L of glucose, and 20 g/L of nutrient agar.

1. Preparation of Mutagenic Starting Strain (1) 200 ul of the bacterial solution of *S. cerevisiae* (hereinafter referred to as wild strain) for producing Huangjiu was taken from a glycerin storage tube, coated on an YPD plate and cultured at 30° C. for 24 h.

(2) A single colony was picked with an inoculating loop and inoculated to a shake flask containing 100 ml of YPD liquid medium, and cultured at 30° C. and 200 r/min for 24 h.

(3) 5 ml of the obtained bacterial solution was inoculated into the shake flask containing 100 ml of YPD liquid medium, and cultured at 30° C. and 200 r/min, the OD600 of the bacterial solution was measured every other hour, after the exponential growth phase of yeast is finished, the OD600 was measured every other 3 h and three samples were taken at a time. The growth curve was drawn, and time at which the starting strain was in a mid-exponential growth phase was determined as the start time of the ultraviolet mutagenesis. The strain at this time was the mutagenic starting strain.

Figure 1:
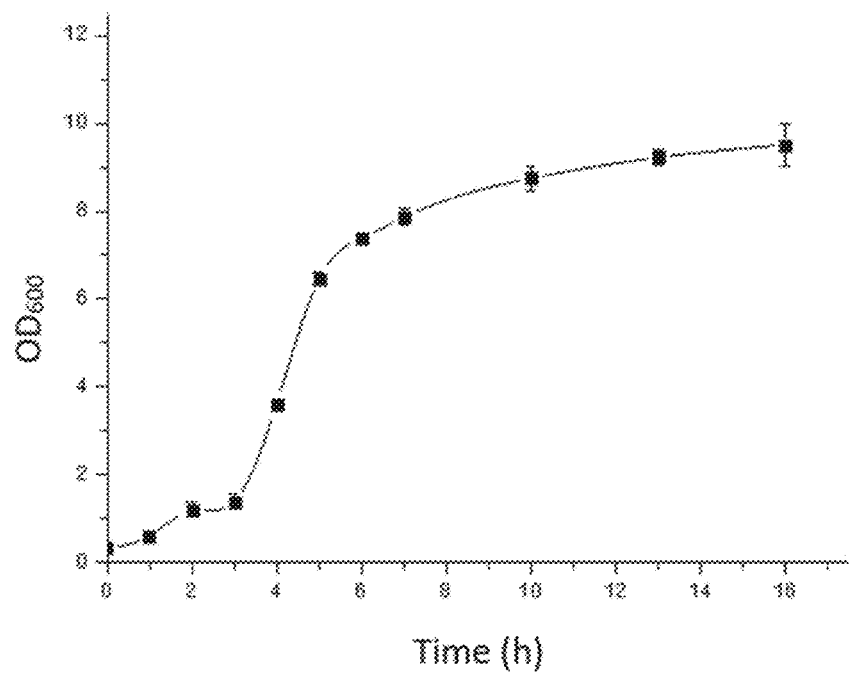
FIG. 1 is a graph showing the growth curve of a starting yeast strain according to Example 1.

The experimental results were shown in FIG. 1: the OD600 value of yeast increased significantly when cultured for 3-5 h, at which time the yeast growth was in the exponential growth phase, and the wild strain was in the mid-exponential growth phase when being cultured on a shaker for 4 h. Therefore, the yeast being cultured on the shaker for 4 h was selected as the mutagenic starting strain.

2. Determination of Ultraviolet Mutagenesis Time (1) The bacterial solution of the mutagenic starting yeast strain was obtained as described in step 1.

(2) 10 ml of the bacterial suspension of the mutagenic starting strain was centrifuged at 6000 r/min for 5 min before the supernatant was removed, 50 ml of physiological saline was added, shaken, mixed well to obtain a bacterial suspension.

(3) Ultraviolet radiation: a UV lamp was firstly turned on for pre-heating for 20 minutes to stabilize the light wave. 4.5 mL of the above bacterial suspension was pipetted into a sterile Petri dish with the diameter being 9 cm using a 5 mL sterile pipette, and a sterile pin was added to the Petri dish. The Petri dish containing the bacterial suspension was placed on a magnetic stirrer, vertically positioned under the UV lamp and irradiated for 20 s, a lid was opened under a dark condition (the UV lamp was ensured to irradiate evenly), and exposed to ultraviolet light (15 W UV lamp, 30 cm apart) for 40 s, 60 s, 80 s, 100 s and 120 s.

(4) After the irradiation was completed, the yeast suspension after mutagenesis was diluted by a 10-fold dilution method under a red light or a dark condition to 4 gradients of 10-1, 10-2, 10-3 and 10-4. 200 μL of each gradient was coated on a YPD plate and wrapped in tin foil to protect from light. The samples were cultured at 30° C. for 48 h in triplicate.

(5) The unmutated yeast suspension was diluted by a 10-fold dilution method to 5 gradients of 10-1, 10-2, 10-3, 10-4 and 10-5. 200 μL of each gradient was coated on a YPD plate as a control. The control group was cultured at 30° C. for 48 h in triplicate.

(6) The number of colonies was counted via a plate count method and recorded in a table, the lethality rate was calculated, and the lethality rate curve was plotted. The ultraviolet irradiation time was determined when the ultraviolet lethality rate was 70%-80%, 80%-90% and 90%-100% respectively. Wherein lethality rate=(number of colonies in the control group−number of colonies in the mutagenized group)/number of colonies in the control group.

Figure 2:
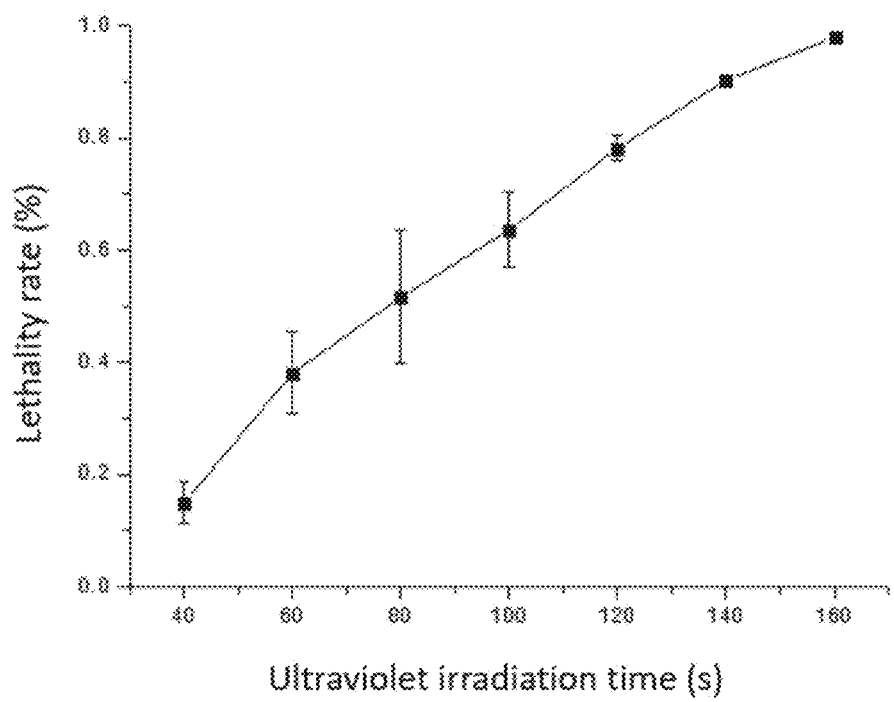
FIG. 2 is a graph showing the lethality rate curve of ultraviolet irradiation to the starting yeast strain according to Example 1.

Experimental results: Mutagenic starting strain was subjected to ultraviolet mutagenesis, and different concentrations of the gradient suspension were coated on YPD plates. The lethality rate curve was plotted according to the number of growth colonies. The results are shown in FIG. 2. According to the lethality rate curve, the irradiation time was 110 s, 130 s and 150 s when the lethality rate was 70%-80%, 80%-90% and 90%-100% respectively.

3. Determination of the Lowest Total Lethal Concentration of p-Fluorophenylalanine YNBP solid medium: 6.7% of YNB, 20 g/L of glucose, 10 g/L of proline, and additional p-fluorophenylalanine at concentrations of 0 (control), 0.04 g/L, 0.05 g/L, 0.06 g/L, 0.07 g/L, 0.08 g/L, 0.09 g/L and 0.1 g/L.

(1) The bacterial suspension in mid-exponential growth phase was diluted by a 10-fold dilution method to 4 gradients of 10-1, 10-2, 10-3 and 10-4, and 200 μL of bacterial suspension at 10-4 gradient was coated on a YNBP plate.

(2) The bacterial suspension was cultured at 30° C. for 48-72 h. The number of colonies was recorded and the lethality rate curve of p-fluorophenylalanine was plotted.

Lethality rate=(number of colonies in the control group−number of colonies in the mutagenized group)/number of colonies in the control group.

Figure 3:
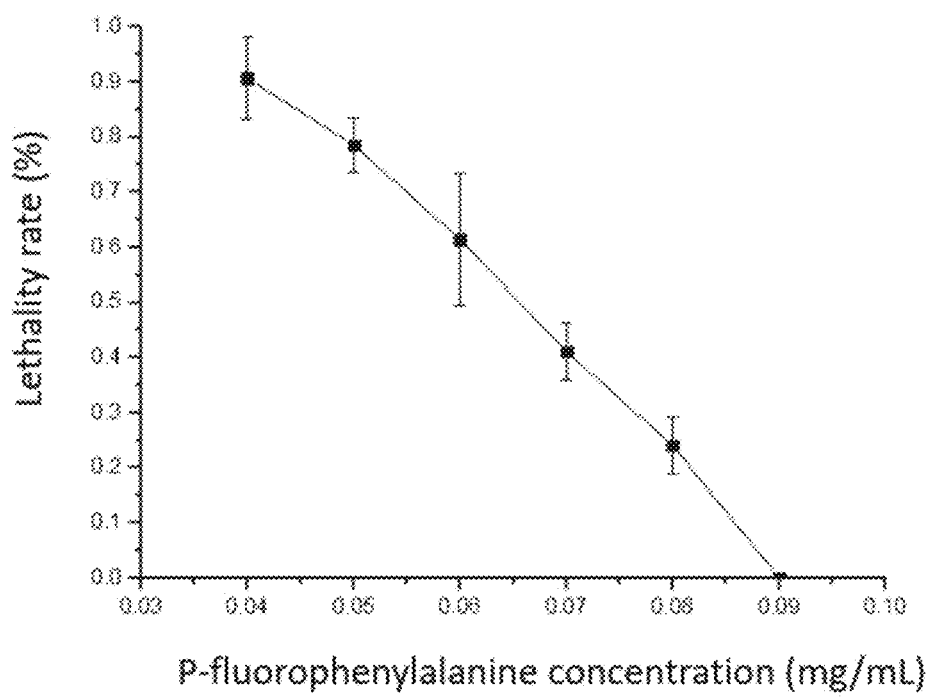
FIG. 3 is a graph showing the lethality rate curve of p-fluorophenylalanine to the starting strain according to Example 1.

Experimental results: The lethality rate curve of p-fluorophenylalanine was shown in FIG. 3. As the concentration of p-fluorophenylalanine on the YNBP plate was increased, the lethality rate of yeast was increased. When the concentration of p-fluorophenylalanine was increased to 0.09 g/L, the yeast was all lethal. Therefore, the lowest total lethal concentration of p-fluorophenylalanine was determined to be 0.09 g/L.

4. Ultraviolet Mutagenesis

The ultraviolet mutagenic starting strains were obtained as described in step 2, and exposed to ultraviolet irradiation. The total times of ultraviolet mutagenesis were 110 s, 130 s and 150 s respectively.

5. p-Fluorophenylalanine Resistance Screening and Alcohol Tolerance Screening (1) p-Fluorophenylalanine Resistance Screening The formula of the medium for p-fluorophenylalanine resistance screening: 6.7% of YNB, 20 g/L of glucose, 10 g/L of proline, 0.09 g/L of p-fluorophenylalanine, and 20 g/L of nutrient agar.

200 μL of the ultraviolet mutagenic bacterial suspension was coated on a plate for p-fluorophenylalanine resistance screening, and wrapped in tin foil to protect from light. Three plates were carried out for each lethality rate and cultured at 30° C. for 72 h.

(2) Alcohol Tolerance Screening

The formula of the medium for alcohol screening: 10 g/L of yeast extract, 20 g/L of peptone, fish powder, 20 g/L of glucose, and 10% of sterile ethanol.

1) Each well of a 96-well plate was added with 20 μL of YPD liquid medium. The mutant strains after p-fluorophenylalanine resistance screening were inoculated into the wells, and cultured at 30° C. for 24 h.

2) Each well of a 96-well plate was added with 200 μL of alcohol screening medium. The seed solution of each well in the previous step was inoculated into the well plate at the amount of 5%, and cultured at 30° C. under static condition. OD600 was measured by a microplate reader at 12 h and 24 h respectively.

3) The $OD600_{12\,h}$, $OD600_{24\,h}$ and $OD600_{24\,h}-OD600_{12\,h}$ values were calculated, and a total of 22 mutagenized yeast strains with relatively high values were selected.

6. Huangjiu Simulated Liquid Fermentation Screening

Preparation of Huangjiu simulated liquid: 1 kg of steamed rice (with water content of 70%) was added with 1 L of water and 0.05 kg of wheat qu. The mixture was stirred well, incubated at 60° C. for 8 h and centrifuged at 4500 r/min for 5 min. The supernatant was taken and sterilized at 115° C. for 15 min.

(1) 22 mutant strains were streaked onto YPD plates and cultured at 30° C. for 24 h.

(2) The single colony was picked, inoculated into a 50 ml centrifuge tube containing 10 ml of YPD, and cultured at 30° C. and 200 r/min for 12 h.

(3) 5% of the bacterial solution was pipetted, inoculated into a 50-centrifuge tube containing 20 ml of Huangjiu simulated liquid, and statically fermented at 30° C. for 7 d in triplicate.

(4) High performance liquid chromatography was used to determine the content of β-phenylethanol in Huangjiu simulated liquid, and the strain with relatively high β-phenylethanol content was screened.

High Performance Liquid Chromatography Analysis:

1) 2 mL of the sample was placed in a 2 mL centrifuge tube and centrifuged at 12,000 rpm for 1 min to remove the bacteria.

2) 1 mL of the supernatant was taken, passed through a 0.22 μm aqueous membrane and transferred to a vial of liquid phase for future use.

3) X-bridge C18 column was used, the mobile phase was methanol and pure water at the ratio of 1:1, the sample was injected at 30° C. at a flow rate of 1 mL/min and the injection volume was 10 ul.

The content of β-phenylethanol in the simulated fermentation broth of Huangjiu was determined by high performance liquid chromatography. The 1-e4 mutant strain had relatively high average content of 3-phenylethanol, which was 185.032 mg/L as shown in Table 1, and excellent alcohol production capacity. Therefore, the strain was used as the starting strain for the next round of normal temperature isobaric plasma mutagenesis.

TABLE 1

β-phenylethanol content in simulated fermentation broth of Huangjiu after ultraviolet mutagenesis

| Number of strain | β-phenylethanol content (mg/L) | | | Average content of β-phenylethanol (mg/L) | Alcohol content % (v/v) |
|---|---|---|---|---|---|
| | 1 | 2 | 3 | | |
| Wild strain | 38.334 | 35.558 | 29.157 | 34.350 | 8.1 |
| 1-a6 | 51.412 | 72.991 | 47.68 | 57.361 | 7.2 |
| 1-b11 | 44.24 | 47.705 | 47.763 | 46.569 | 6.1 |
| 1-b7 | 90.335 | 95.223 | 90.551 | 92.036 | 8.2 |
| 1-c3 | 53.372 | 44.549 | 47.611 | 48.511 | 7.8 |
| 1-d3 | 152.466 | 142.493 | 155.337 | 150.099 | 7.3 |
| 1-e3 | 61.769 | 47.129 | 44.157 | 51.018 | 6.8 |
| 1-e4 | 183.653 | 191.539 | 179.904 | 185.032 | 7.9 |
| 1-F7 | 42.272 | 42.546 | 46.282 | 43.700 | 7.4 |
| 1-g3 | 37.716 | 41.4 | 39.175 | 39.430 | 7.5 |
| 2-a1 | 43.536 | 30.122 | 35.137 | 36.265 | 7.6 |
| 2-c11 | 183.101 | 176.583 | 159.214 | 172.966 | 6.8 |
| 2-c4 | 48.825 | 47.999 | 45.159 | 47.328 | 7.9 |
| 2-c6 | 47.069 | 51.12 | 52.127 | 50.105 | 8.2 |
| 2-d1 | 38.687 | 54.652 | 39.37 | 44.236 | 6.5 |
| 2-e10 | 137.207 | 145.772 | 144.723 | 142.567 | 7.8 |
| 2-e5 | 60.119 | 60.282 | 41.639 | 54.013 | 7.4 |
| 2-f10 | 37.666 | 38.732 | 52.325 | 42.908 | 6.7 |
| 2-f2 | 39.56 | 43.969 | 46.512 | 43.347 | 7.4 |
| 2-f6 | 140.492 | 144.677 | 141.238 | 142.136 | 7.5 |
| 2-f7 | 48.259 | 51.973 | 51.999 | 50.744 | 6.4 |
| 2-g7 | 180.908 | 184.357 | 175.521 | 180.262 | 6.7 |
| 2-h1 | 47.482 | 44.733 | 52.107 | 48.107 | 7.4 |

Example 2: Normal Temperature Isobaric Plasma Mutagenesis and Screening

1. Normal Temperature Isobaric Plasma Mutagenesis and Huangjiu Simulated Liquid Fermentation Screening After the first round of ultraviolet mutagenesis, the selected strain 1-e4 was used as a starting strain for normal temperature isobaric plasma mutagenesis. The 1-e4 strain was cultured in a YPD shake flask at 30° C. for 24 h, and the bacterial suspension with OD600 of 0.6-0.8 was prepared with physiological saline. The normal temperature isobaric plasma mutagenesis was carried out. The mutagenesis time was 60 s and the power was 100 w. After mutagenesis, the strain was resuspended to form a bacterial solution, diluted, coated on a YPD plate, and cultured at 30° C. for 48 h. The single colony was streaked onto a YNBP plate (concentration of p-fluorophenylalanine was 0.5 g/L), and the strain with good growth vigour on YNBP plate was subjected to Huangjiu simulated liquid fermentation screening. The content of β-phenylethanol in simulated liquid of Huangjiu was determined by high performance liquid chromatography, and the strain with relatively high β-phenylethanol content was screened.

The content of β-phenylethanol in the simulated fermentation broth of the Huangjiu fermented for 8 d was determined by high performance liquid chromatography. The average contents of β-phenylethanol in the 3-c10, 4-c7 and 5-f5 mutant strains were relatively high, which were 217.192 mg/L, 257.388 mg/L and 337.168 mg/L respectively. The three strains were named as BYC1, BYC2 and BYC3 respectively. The β-phenylethanol yield of S. cerevisiae was increased. Although the ethanol yield of S. cerevisiae was slightly decreased after mutagenesis, alcoholic fermentation could still be carried out well by obtained S. cerevisiae.

TABLE 2

β-phenylethanol content in simulated fermentation broth of Huangjiu after normal temperature isobaric plasma mutagenesis

| Number of strain | β-phenylethanol content (mg/L) | | | Average content of β-phenylethanol (mg/L) | Alcohol content % (v/v) |
|---|---|---|---|---|---|
| | 1 | 2 | 3 | | |
| Starting strain (1-e4) | 207.360 | 186.934 | 173.654 | 189.316 | 8.8 |
| 3-a1 | 157.521 | 157.498 | 159.742 | 158.254 | 8.5 |
| 3-b10 | 158.003 | 154.591 | 150.313 | 154.302 | 7.9 |
| 3-b7 | 135.600 | 131.841 | 148.140 | 138.527 | 8.4 |
| 3-c10 | 214.345 | 227.563 | 209.667 | 217.192 | 8.5 |
| 3-c9 | 139.127 | 140.839 | 145.957 | 141.974 | 7.2 |
| 3-d5 | 140.569 | 138.511 | 144.225 | 141.102 | 7.5 |
| 3-d7 | 150.91 | 171.061 | 144.091 | 155.354 | 9.5 |
| 3-d9 | 142.133 | 143.046 | 146.896 | 144.025 | 8.9 |
| 3-e11 | 143.821 | 140.809 | 146.813 | 143.814 | 6.8 |
| 3-e9 | 142.946 | 146.638 | 140.704 | 143.429 | 9.4 |
| 3-f7 | 42.462 | 47.457 | 45.899 | 45.273 | 9.3 |
| 3-f9 | 172.211 | 142.423 | 136.002 | 150.212 | 7.1 |
| 3-g6 | 33.933 | 34.995 | 48.254 | 39.061 | 9.7 |
| 4-a8 | 138.400 | 139.363 | 140.223 | 139.329 | 8.5 |
| 4-a9 | 137.822 | 130.866 | 134.799 | 134.496 | 8.3 |
| 4-c7 | 270.921 | 249.241 | 252.003 | 257.388 | 8.1 |
| 4-d4 | 136.006 | 144.753 | 139.349 | 140.036 | 8.4 |
| 4-d7 | 150.539 | 169.307 | 150.479 | 156.775 | 8.9 |
| 4-e2 | 145.356 | 138.507 | 150.109 | 144.657 | 8.8 |
| 4-e4 | 155.774 | 146.430 | 144.465 | 148.890 | 9.4 |
| 4-e8 | 49.119 | 61.005 | 51.411 | 53.845 | 8.9 |
| 4-f2 | 50.124 | 47.689 | 44.800 | 47.538 | 9.2 |
| 4-f4 | 42.619 | 42.050 | 61.006 | 48.558 | 9.3 |
| 4-f7 | 44.467 | 54.139 | 60.876 | 53.161 | 8.8 |
| 4-f9 | 140.081 | 148.839 | 138.319 | 142.413 | 8.3 |
| 4-g11 | 38.139 | 38.063 | 37.475 | 37.892 | 9.1 |
| 5-a5 | 61.535 | 56.455 | 59.965 | 59.318 | 9.3 |
| 5-c5 | 163.834 | 157.544 | 164.466 | 161.948 | 8.2 |
| 5-f5 | 328.942 | 346.023 | 336.538 | 337.168 | 8.3 |

2. Huangjiu Fermentation Screening

Preparation of seeding yeast: the yeast strain was inoculated into a 50 mL YPD shake flask, cultured at 30° C. and 200 r/min for 24 h. 1 kg of steamed rice (with the water content of 70%) was added with 1 L of water and 0.05 kg of wheat qu. The mixture was stirred well and incubated at 60° C. for 4 h. After cooling, the yeast solution was inoculated at the amount of 5% and cultured at 30° C. and 200 r/min for 16 h.

(1) Ingredients

The steamed rice (with the water content of 70%) was added with equal amount of fresh water, 2% of wheat qu, and 5% of seeding yeast, and the mixture was stirred well.

(2) Fermentation and Stirring

The fermentation temperature was 28° C., and the samples were stirred and taken at 18 h, 24 h, 30 h, 42 h, 54 h, 78 h and 126 h after completing formulation. A supernatant sample was obtained by centrifugation at 5000 r/min for 10 min for index detection.

(3) Index Detection

The samples taken at 18 h, 24 h, 30 h, 42 h, 54 h, 78 h and 126 h were measured for total acid (in terms of lactic acid), alcohol content and pH. The changes of the three indexes were observed and the β-phenylethanol content in the sample taken at 126 h was determined by high performance liquid chromatography.

Figure 4:
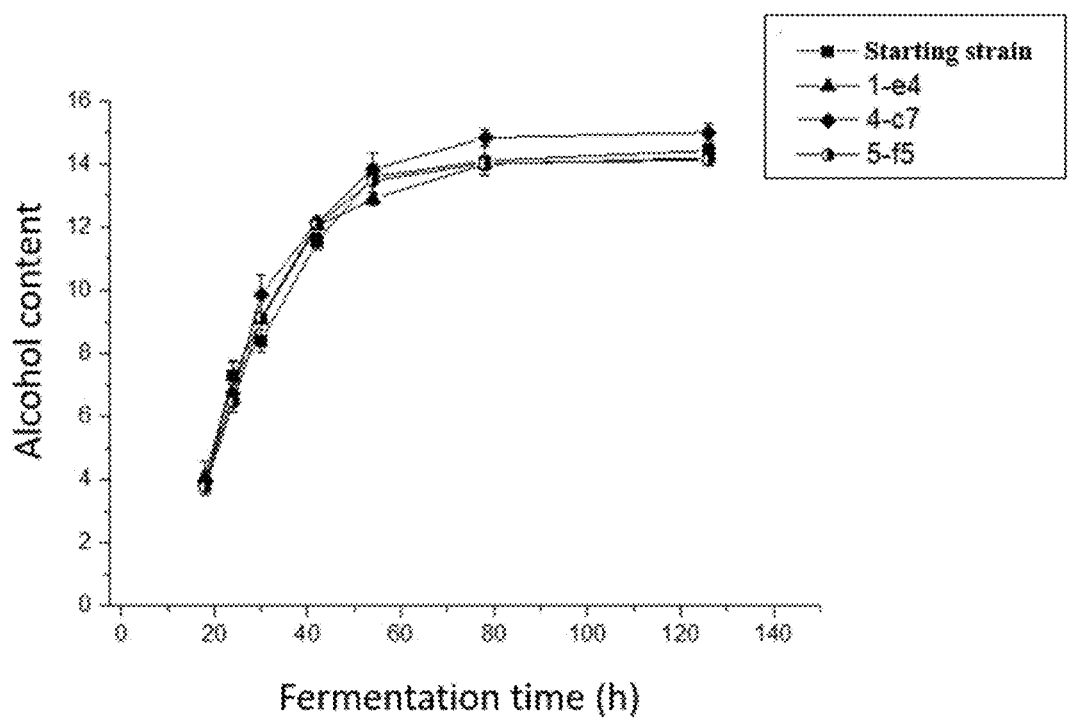
FIG. 4 is a graph showing the change curve of alcohol content during Huangjiu fermentation according to Example 2.
Figure 5:
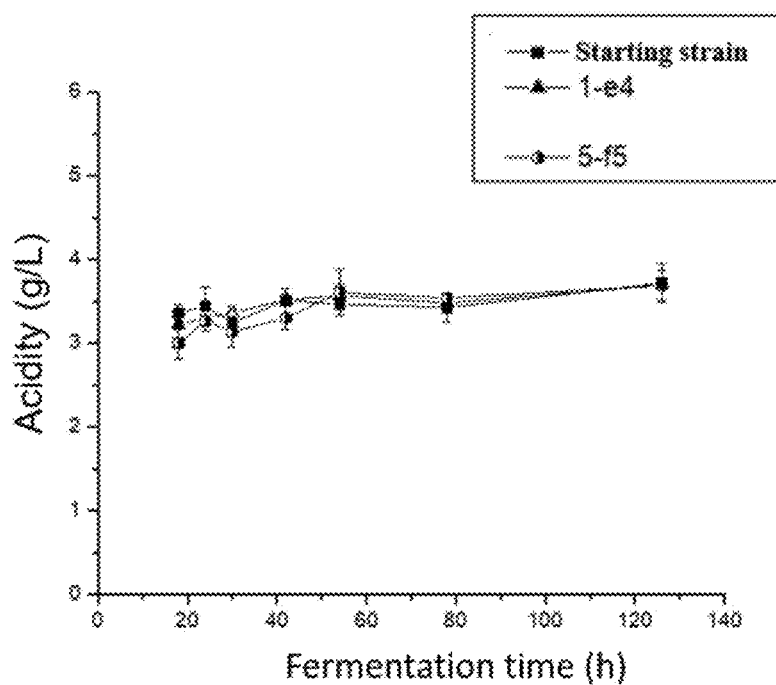
FIG. 5 is a graph showing the change curve in acidity during Huangjiu fermentation according to Example 2.
Figure 6:
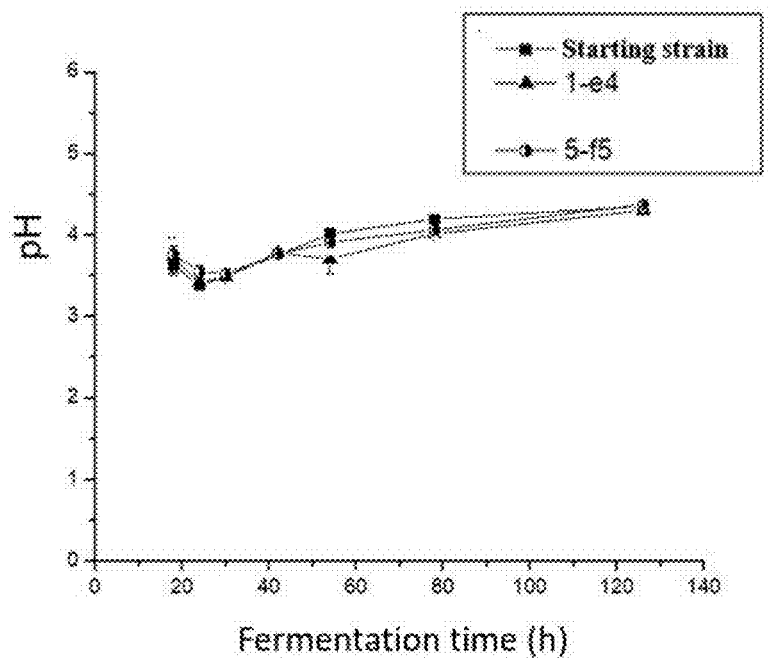
FIG. 6 is a graph showing the pH change curve during Huangjiu fermentation according to Example 2.

The Huangjiu was fermented by the starting strain in the current round of mutagenesis and three mutant yeast strains as screened, and the results of alcohol production capacity were shown in FIG. 4. Comparing the three positive-mutation strains with the starting strain, there was a small difference in alcohol production capacity, the alcohol contents were 13% (v/v) or above, and the alcoholic fermentations were good. For the three yeast strains, the alcoholic fermentation was rapid in the first 60 h, and the alcohol content was basically stable after 60 h. The acidity change results were shown in FIG. 5. The acidity of the Huangjiu fermented by three mutant yeast strains was between 3-4 g/L. As the fermentation proceeded, the acidity increased slightly and tended to be gentle. The pH changes were shown in FIG. 6. The pH values were between 3-4.5 and the alcoholic fermentation could be performed well by S. cerevisiae.

The content of β-phenylethanol in the fermentation broth of Huangjiu was shown in Table 3 below. The Huangjiu was fermented with BYC1, BYC2 and BYC3 strains. The β-phenylethanol contents were 219.08, 254.91 and 365.70 mg/L. The β-phenylethanol content in the Huangjiu fermented by the starting strain was only 188.07 mg/L. The β-phenylethanol yields of the three strains were 1.16 times, 1.35 times and 1.94 times higher than that of the starting strain respectively, and the three strains had good ability to produce high concentration of β-phenylethanol.

TABLE 3

β-phenylethanol content in fermentation broth of Huangjiu after normal temperature isobaric plasma mutagenesis

| Name of strain | β-phenylethanol content (mg/L) | | | Average content of β-phenylethanol (mg/L) | β-phenylethanol yield of re-screened strain/β-phenylethanol yield of starting strain |
|---|---|---|---|---|---|
| | 1 | 2 | 3 | | |
| Staring strain (1-e4) | 189.56 | 198.80 | 175.85 | 188.07 | 1 |
| BYC1 | 212.85 | 220.64 | 223.74 | 219.08 | 1.16 |
| BYC2 | 256.13 | 263.36 | 245.24 | 254.91 | 1.35 |
| BYC3 | 358.40 | 365.03 | 373.69 | 365.70 | 1.94 |

Isobutanol, isoamyl alcohol, 2-phenylethyl acetate and glycerin in the fermentation broth of Huangjiu were used as flavor substances to improve the overall quality of Huangjiu, and their contents were shown in Table 4. By comparison, the contents of 2-phenylethyl acetate and glycerin of BYC3 strain were significantly higher than that of the starting strain as well as BYC1 and BYC2.

TABLE 4

Contents of isobutanol, isoamyl alcohol, 2-phenylethyl acetate and glycerin in fermentation broth of Huangjiu

| Name of strain | Isobutanol (mg/L) | Isoamyl alcohol (mg/L) | 2-phenylethyl acetate (μg/L) | Glycerin (g/L) |
|---|---|---|---|---|
| Staring strain (1-e4) | 46.32 | 116.32 | 12.23 | 4.21 |
| BYC1 | 57.25 | 132.65 | 16.15 | 4.08 |
| BYC2 | 66.37 | 157.37 | 21.66 | 5.34 |
| BYC3 | 73.54 | 183.45 | 26.86 | 6.34 |

Figure 7:
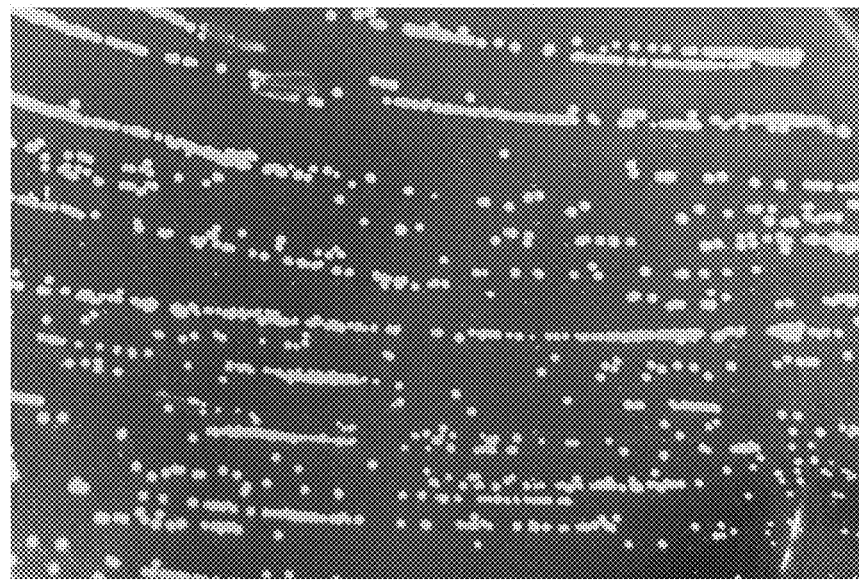
FIG. 7 is a colony morphology of *S. cerevisiae* BYC3 according to Example 2.

In summary, BYC3 had a high yield of β-phenylethanol, and high contents of isobutanol, isoamyl alcohol and 2-phenylethyl acetate. The BYC3 strain was streaked onto a YPD solid medium plate and cultured at 30° C. for 24 h. The colony morphology was shown in FIG. 7. The BYC3 strain was deposited in China Center for Type Culture Collection with the accession number of CCTCC NO: M 2016785. The BYC3 strain was inoculated into the Huangjiu fermentation system, and the alcoholic fermentation performance was good. The β-phenylethanol content of the obtained Huangjiu was 365.70 mg/L.

3. Comparative Experiment of Yeast Strain Producing High Concentration of 3-Phenylethanol in YPD Medium BYC3 strain (i.e. CCTCC NO: M 2016785), wild strain, commercial active dry yeast, S. cerevisiae type strain W303 (genotype: Mat a/a, ura3-1, leu2-3, 112, trp1-1, his3-11, 15, ade2-1 and can1-100), and S. cerevisiae type strain S288c (genotype: MATα SUC2 gal2 mal2 mel flo1 flo8-1 hap1 ho bio1 bio6) were subjected to comparative fermentation experiments. The five strains were activated by a YPD plate before inoculated into YPD shake flasks, and then sequentially inoculated into the YPD shake flasks and YPD shake flasks containing 1 g/L of phenylalanine at the amount of 5%.

Figure 8:
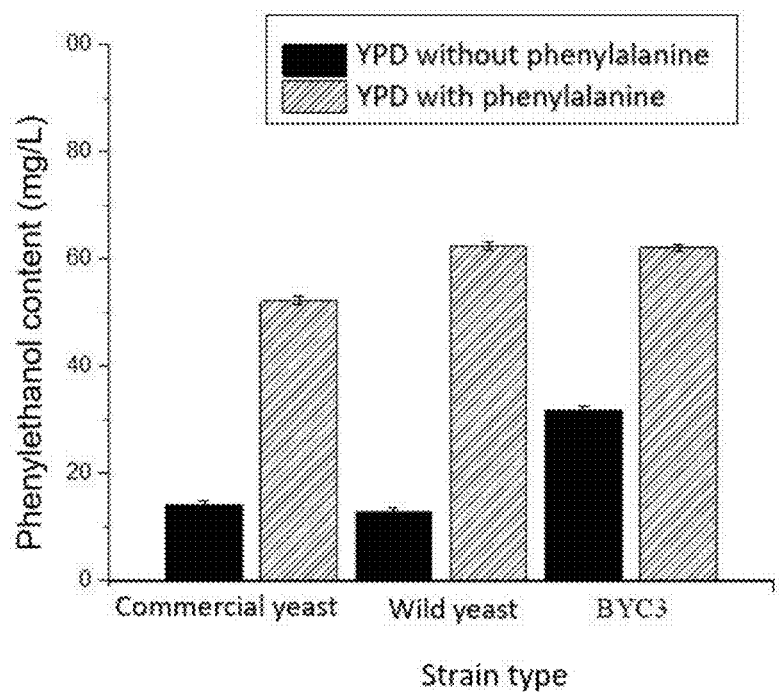
FIG. 8 is a graph showing the β-phenylethanol yield of the strain *S. cerevisiae* M 2016785 in YPD according to Example 2.

The experimental results were shown in FIG. 8. The β-phenylethanol yield of S. cerevisiae strain BYC3 was significantly higher than that of wild strain, commercial active dry yeast, W303 and S288c. The β-phenylethanol yield of BYC3 yeast in YPD medium reached 31.6 mg/L, which was 50.9% of the yield when adding 1 g/L of phenylalanine (21% for wild yeast, 27% for commercial yeast, 22% for W303, and 20% for S288c). The yeast BYC3 had excellent β-phenylethanol production capacity, which was significantly higher than that of existing S. cerevisiae strains.

Example 3: Application of the Yeast Producing High Concentration of β-Phenylethanol in Huangjiu 1. Huangjiu Brewing Process I (1) Preparation of seeding yeast: The yeast strain was inoculated into a 50 mL YPD shake flask and cultured at 30° C. and 200 r/min for 24 h. 1 kg of steamed rice (wi the water content of 70%) was added with 1 L of water and 0.05 kg of wheat qu. The mixture was stirred well and incubated at 60° C. for 4 h. After cooling, a yeast solution was inoculated at the amount of 5% and cultured at 30° C. and 200 r/min for 16 h. The S. cerevisiae BYC3 (i.e. CCTCC NO: M 2016785) producing high concentration of 1-phenylethanol was selected as the yeast.

(2) The steamed rice (with the water content of 40%) was added with equal amount of fresh water, 15% of wheat qu and 5% of seeding yeast. The mixture was stirred well.

(3) Fermentation and stirring: The fermentation temperature was 28° C. and the timing was started after completing blanking. The stirring was performed every other 8 hours for 6 times. Fermentation was performed for 5-7 days and terminated until the alcohol content index was no longer elevated.

(4) Pressing: After completing fermentation, the fermenting mash was pressed through a plate-and-frame filter to obtain fine rice wine.

(5) Sterilization: The fine rice wine was sterilized through a sterilizer at 85° C. for 30 min.

(6) Aging: After sterilizing, the fine rice wine was aged in an aging tank for 6 months.

(7) Filtration: After aging, the fine rice wine was filtered through a diatomaceous earth filter and a membrane filter to remove infectious microbes and impurities.

(8) Sterilization and filling: The fine rice wine was sterilized through a sterilizer at 85° C. for 30 min and subjected to hot filling.

The high performance liquid chromatography was used to detect the obtained product that β-phenylethanol content was up to 410 mg/L, alcohol content was 17% (v/v), ethyl acetate content was 24 mg/L, and 2-phenylethyl acetate content was 56 μg/L.

2. Huangjiu Brewing Process II (1) Preparation of seeding yeast: The seeding yeast was prepared as described in the above process I of the present example.

(2) Smash of glutinous rice: Fresh water was added in an amount of 2.5 times the weight of glutinous rice. High temperature gelatinization was carried out on high temperature amylase at 110° C. for 40 min. After cooling to 35° C., glucoamylasee was added, and saccharification was carried out for 40 min. After cooling to 28° C., 4% of wheat qu by total volume and 10% of seeding yeast by total volume were added. The mixture was stirred well.

(3) The remaining steps are as described in the above process I of the present example.

The high performance liquid chromatography was used to detect the obtained product that β-phenylethanol content was up to 185 mg/L, alcohol content was 14% (v/v), ethyl acetate content was 14 mg/L, and 2-phenylethyl acetate content was 24 μg/L.

3. Comparative Experiment of Yeast Strain Producing High Concentration of β-Phenylethanol in Fermenting Mash of Huangjiu BYC3 strain, wild strain, commercial active dry yeast, *S. cerevisiae* type strain W303 (genotype: Mat a/a, ura3-1, leu2-3, 112, trp1-1, his3-11, 15, ade2-1 and can1-100), and *S. cerevisiae* type strain S288c (genotype: MATα SUC2 gal2 mal2 mel flo1 flo8-1 hap1 ho bio1 bio6) were subjected to comparative fermentation experiments. The Huangjiu brewing method for the five strains was as described in the above Huangjiu brewing process I of the present example.

The results were as follows: β-phenylethanol yield (410 mg/L) of *S. cerevisiae* strain BYC3 was significantly higher than that of wild strain (82 mg/L), commercial active dry yeast (87 mg/L), W303 (81 mg/L) and S288c (73 mg/L). The alcohol content of the *S. cerevisiae* strain BYC3 reached 17% (v/v), and alcohol contents of the commercial active dry yeast, W303 and S288c were 16.5% (v/v), 12.4% (v/v) and 13.1% (v/v) respectively. It indicated that the strain BYC3 had excellent β-phenylethanol production capacity, which was significantly higher than the existing *S. cerevisiae* strain and also had strong alcohol production capacity. The concentration of 2-phenylethyl acetate produced by yeast strain BYC3 reached 56 μg/L, which was 4.5 times that of wild strain, 4.3 times that of commercial active dry yeast, 5 times that of W303, and 5.7 times that of S288c. The concentration of isoamyl alcohol produced by the yeast strain BYC3 was 1.7 times that of the wild strain, 1.8 times that of the commercial active dry yeast, 2.1 times of the W303, and 2.4 times that of the S288c.

Example 4: Application of the Yeast Producing High Concentration of 3-Phenylethanol in Cooking Wine 1. Cooking Wine Brewing Process I The Huangjiu was obtained according to the Huangjiu brewing process I in Example 3 and 10% of salt was added. The mixture was sterilized through a sterilizer at 85° C. for 30 min and subjected to hot filling.

The high performance liquid chromatography was used to detect the obtained product that β-phenylethanol content was up to 450 mg/L, alcohol content was 15% (v/v), ethyl acetate content was 20 mg/L, and 2-phenylethyl acetate content was 50 μg/L.

2. Huangjiu Brewing Process II

The Huangjiu was obtained according to the Huangjiu brewing process II in Example 3 and 10% of salt was added. The mixture was sterilized through a sterilizer at 85° C. for 30 min and subjected to hot filling. The β-phenylethanol content reached 140 mg/L, the alcohol content was 12% (v/v), the ethyl acetate content was 10 mg/L, and the 2-phenylethyl acetate content was 20 μg/L.

Example 5: Application of the Yeast Producing High Concentration of β-Phenylethanol in Solid-State Fermentation of Brewing Vinegar The Huangjiu, fermented by the process I of Example 3, was used as a raw material for acetic fermentation.

The solid-state fermentation process was used for acetic fermentation. The Chinese crude bran, bran and Huangjiu were mixed well in a ratio of 1:4:10, and 5% of vinegar culture was inoculated. The culture was turned from the surface of the material every day for 1-2 days after inoculation. The temperature was 35-40° C. On days 6-8, the culture was turned to the bottom of the material. On days 8-12, the culture was turned from the bottom every day and the temperature was naturally lowered. The raw vinegar was separated from the vinegar culture and aged for 12 months after being sterilized at 85° C. for 30 min. The obtained product was subjected to high temperature sterilization before hot filling.

The brewing vinegar obtained by solid-state fermentation had an acetic acid content of 60 g/L, a β-phenylethanol content of up to 300 mg/L, and a 2-phenylethyl acetate content of 45 μg/L.

Example 6: Application of the Yeast Producing High Concentration of 8-Phenylethanol in Liquid-State Fermentation of Brewing Vinegar The Huangjiu, fermented by the process I of Example 3, was used as a raw material for acetic fermentation.

The liquid-state fermentation process was used for acetic fermentation. The Huangjiu was diluted 4 times with fresh water, and 5% of cultured acetic acid bacteria solution was inoculated. The mixture was introduced with oxygen at 1 L/min and stirred. When the alcohol content in the fermentation system was less than 1%, the Huangjiu was added in batches. The alcohol content in the acetic fermentation system was controlled at 1%-4%. When the acetic acid content in the fermentation system was about 80 g/L, the mixture was centrifuged to obtain liquid vinegar. The obtained product was subjected to high temperature sterilization before hot filling. The brewing vinegar obtained by liquid-state fermentation had a β-phenylethanol content of up to 100 mg/L, and a 2-phenylethyl acetate content of 36 μg/L.

Example 7: Application of the Yeast Producing High Concentration of 3-Phenylethanol in High-Salt Dilute-State Fermentation of Brewing Soybean Sauce The brewed soybean sauce was fermented by a high-salt dilute-state method, and the soybean meal and wheat were mixed well and steamed in a ratio of 1:1. The *A. oryzae* was inoculated at the amount of 10%, the temperature was controlled at 30° C., and the salt water was added in an amount of 2 times the mass of the material. The sauce mash had a salt content of 18% and a water content of 65%, which was stirred and mixed well. BYC3 yeast was cultured in a YPD shake flask, which was inoculated into part of the steamed and cooled soybean meal and wheat at the amount of 5%. 2 times volume of fresh water was added and the mixture was cultured at 30° C. and 200 r/min for 24 h to produce BYC3 seeding yeast to be added to the sauce mash. The initial fermentation temperature of the sauce mash was 15° C. As the fermentation proceeded, the temperature was increased to 15-35° C. The BYC3 seeding yeast was inoculated when the temperature was increased to 20° C. The fermentation time was 5 months.

After completing fermentation, the sauce mash was pressed through a plate-and-frame filter to remove the sauce mash. After the pressing was finished, diatomaceous earth filtration and membrane filtration were carried out to remove the precipitate. The clarified soybean sauce was filtered, sterilized at 85° C. for 30 min, and subjected to hot filling. The yeast producing high concentration of β-phenylethanol was used for high-salt dilute-state fermentation, and the obtained soybean sauce product had a β-phenylethanol content of 200 mg/L.

Example 8: Application of the Yeast Producing High Concentration of 1-Phenylethanol in Low-Salt Solid-State Fermentation of Brewing Soybean Sauce The brewed soybean sauce was fermented by low-salt solid-state method, and the soybean meal and wheat were mixed well and steamed in a ratio of 1:1. The *A. oryzae* was inoculated at the amount of 10%, the temperature was controlled at 30° C., and the salt water was added in an amount of 2 times the mass of the material. The sauce mash had a salt content of 7% and a water content of 40%, which was stirred and mixed well. BYC3 yeast was cultured in a YPD shake flask, which was inoculated into part of the steamed and cooled soybean meal and wheat at the amount of 5%. 1 times volume of fresh water was added and the mixture was cultured at 30° C. and 200 r/min for 24 h to produce BYC3 seeding yeast to be added to the sauce mash fermentation system. The temperature was controlled at 40° C. The fermentation time was 15 d.

After completing fermentation, impurities and precipitates were removed from sauce mash. The clarified soybean sauce was filtered, sterilized at 85° C. for 30 min, and subjected to hot filling. The yeast producing high concentration of β-phenylethanol was used for high-salt dilute-state fermentation, and the obtained soybean sauce product had a β-phenylethanol content of 50 mg/L.

Example 9: Application of the Yeast Producing High Concentration of β-Phenylethanol in Baijiu 1. Baijiu Brewing Process I Two rounds of fermentation were used. During the first round of fermentation, the sorghum was steamed, and then subjected to air cooling to 28° C. 4% of *A. oryzae* was added and the mixture was cultured at 28° C. for 24 h. 10% of rice hull, 15% of wheat qu, and 8% of bran were added. BYC3 yeast was inoculated and cultured in a YPD shake flask at the amount of 1%, and the liquor was steamed after 30 days of closed fermentation. At the time of secondary fermentation, 10% of medium-temperature Daqu and BYC3 yeast inoculated and cultured in the YPD shake flask at the amount of 1% were added, and the liquor was steamed after 15 days of fermentation. The two liquors were blended to produce the Baijiu having alcohol content of 65% (v/v), β-phenylethanol content of 110 mg/L, and 2-phenylethyl acetate content of 64 μg/L.

2. Baijiu Brewing Process II

40% of sorghum, 10% of wheat, 5% of corn, 25% of rice, and 20% of glutinous rice were steamed and subjected to air cooling to 25° C. 20% of Chinese crude bran, 20% of wheat qu, and 30% of moisture were added. BYC3 yeast was inoculated and cultured in a YPD shake flask at the amount of 1%. The temperature was 20° C. and the humidity was 70%. The fermentation was carried out for 60 days, and 38% Baijiu was obtained by distillation, in which the content of β-phenylethanol was 50 mg/L and the content of 2-phenylethyl acetate was 26 μg/L.

Example 10: A Brewing Method for Enhancing the Aroma of *Aronia* Wine (1) The *Aronia* fruit was washed, crushed, pressed, and separated by a disc separator to obtain *Aronia* juice.

(2) Sugar was supplemented according to the sugar content of the *Aronia* juice. The supplement amount of white granulated sugar was determined according to the fermentation situation in which 17 g/L sugar would be converted to 1% (v/v) of alcohol content. The mixture was stirred well.

(3) 160 mg/L of potassium pyrosulfite and 100 mg/L of pectinase were fed into the tank and stirred well.

(4) Seed solution activation: *S. cerevisiae* M 2016785 was cultured in a YPD medium under static condition at 28° C. for 12 to 24 h, which was inoculated into the juice containing 50 g/L of sugar at the amount of 5% and cultured under static condition at 28° C. for 16 h or longer.

(5) The activated seed solution was inoculated into the fermentation tank for pre-fermentation. After inoculation, the temperature was controlled at 23-25° C. After 12-24 h, the fermentation was started, and then the temperature was controlled at 20-23° C. Alcohol content, residual sugar, acidity and pH were measured every other 24 h.

(6) When the amount of residual sugar was less than 60 g/L, whether it is necessary to supplement white granulated sugar and supplement amount were determined according to the fermentation situation in which 17 g/L sugar would be converted to 1% (v/v) of alcohol content so that the alcohol content of the juice fermentation could reach the requirement. When the amount of residual sugar was about 4 g/L, the surface of the liquor was calm and the bubbles were less. When the upper layer of liquor was clear, the pre-fermentation was finished. The pre-fermentation time was about 10 d.

(7) After completing the pre-fermentation, the fermentation broth was filtered through diatomaceous earth, and 0.04 g/L of sulfur dioxide was added to the fermentation broth for post-fermentation.

(8) The post-fermentation temperature was controlled below 20° C. 2% of a bentonite clarifying agent was added and fully mixed for about 20 d.

(9) Filtration: After completing the clarification under static condition, the liquor at the bottom of the fermentation tank was drained. The upper liquid was filtered through diatomaceous earth, and then subjected to microfiltration using a membrane filter.

After fermentation, the content of β-phenylethanol was determined by liquid chromatography. The β-phenylethanol content of *Aronia* wine fermented by *S. cerevisiae* (Angel Yeast Co., Ltd) was 61 mg/L, while the β-phenylethanol content of *Aronia* wine fermented by *S. cerevisiae* M 2016785 was up to 350 mg/L.

Example 11: A Brewing Method for Enhancing the Aroma of Fruit Wine Using Lyophilized Powder of *S. cerevisiae* M 2016785

The activated seed solution of *S. cerevisiae* M 2016785 was used in Example 10; while 2% of lyophilized powder of *S. cerevisiae* M 2016785 was added in the present example. The dried bacteria were fully hydrated and defoamed by stirring at 38° C. for 30-60 min. The other steps were the same as those in Example 10. The obtained fruit wine had a 1-phenylethanol content of 325 mg/L.

Wherein, the results of Example 10 and *Aronia* wine fermented by different strains were shown in Table 5.

TABLE 5

Comparison of the results of Aronia wine fermented by different strains

| Strain | Alcohol content (v/v) | Residual sugar (g/L) | β-phenylethanol (mg/L) |
|---|---|---|---|
| Angel Wine *S. cerevisiae* Rv171 (commercial yeast) | 12.6 | 3.88 | 61 |
| *S. cerevisiae* M 2016785 | 12.8 | 3.54 | 350 |
| *S. cerevisiae* M 2016785 lyophilized powder | 12.5 | 3.90 | 325 |
| *S. cerevisiae* type strain W303 | 10.5 | 34.56 | 34 |
| *S. cerevisiae* type strain S288c | 8.6 | 68.15 | 21 |

Example 12: A Brewing Method for Enhancing the Aroma of Hawthorn Wine

The pectin content of hawthorn fruit was as high as 3%-7%, and the fruit was in a gel state after being broken. Therefore, 40-50° C. warm water can be added during the crushing in step (1) of Example 10, and the water quantity was controlled within 1 times the amount of hawthorn. After boiling by heating for 5 minutes, the juice was extracted. The sugar content and acidity of the pulp were adjusted according to the alcohol content requirement of the finished wine during the boiling process. After the finish of the extraction, the temperature of the pulp was lowered to about 40° C. Pectinase and SO2 were added, and the device was stirred well as a juice for fermentation. The other steps were as described in Example 10. The obtained hawthorn wine had a β-phenylethanol content of 243 mg/L and an alcohol content of up to 13% (v/v).

Example 13: A Brewing Method for Enhancing the Aroma of Mulberry Wine

The raw material in Example 10 was changed to mulberry, and the other steps were as described in Example 10. The obtained mulberry wine had a β-phenylethanol content of 305 mg/L and an alcohol content of 13.5% (v/v).

Example 14: A Brewing Method for Enhancing the Aroma of Bayberry Wine

The raw material in Example 10 was changed to bayberry, and the other steps were as described in Example 10. The obtained bayberry wine had a β-phenylethanol content of 212 mg/L and an alcohol content of 14.5% (v/v).

What is claimed is:

1. A fermented food comprising a *Saccharomyces cerevisiae* strain M 2016785, which was deposited in China Center for Type Culture Collection (CCTCC) with accession number of M 2016785, or a microbial agent comprising the *S. cerevisiae* strain M 2016785,
    wherein the fermented food is produced by the process of fermenting the *S. cerevisiae* strain M 2016785 in a liquid culture, and
    wherein the *S. cerevisiae* strain M 2016785 produces β-phenylethanol in the liquid culture without addition of precursor phenylalanine.

2. The fermented food of claim 1, wherein the fermented food comprises alcohol, vinegar, or soy sauce.

3. The fermented food of claim 2, wherein the alcohol is Huangjiu (rice wine), cooking wine, Baijiu (liquor beverage), or fruit wine.

4. The fermented food of claim 3, wherein the alcohol is Huangjiu (rice wine)
    wherein the Huangjiu is produced by the further process of: adding the fermented *S. cerevisiae* strain M 2016785 to steamed rice for further fermentation under conditions that produce β-phenylethanol, and then pressing the rice to obtain rice wine as a liquid separated from the rice, and
    wherein the amount of β-phenylethanol in the Huangjiu is two to four times higher as compared with Huangjiu made from wild type yeast under similar conditions.

5. The fermented food of claim 3, wherein the alcohol is cooking wine which is produced by adding up to 10% salt to the Huangjiu, and
    wherein the amount of β-phenylethanol in the cooking wine is two to four times higher as compared with cooking wine made from wild type yeast under similar conditions.

6. The fermented food of claim 3, wherein the alcohol is vinegar, which is produced by acetic fermentation of the Huangjiu in the presence of bran and vinegar culture, and
    wherein the vinegar has a β-phenylethanol content of at least 300 mg/L.

7. The fermented food of claim 3, wherein the alcohol is Baijiu, and wherein in the fermenting step the *S. cerevisiae* strain M 2016785 is fermented with steamed sorghum and one or more of: rice hull, wheat, corn, rice, and bran, to produce a first liquor, and further comprising the steps of:
    steaming the first liquor to produce a steamed first liquor,
    fermenting the first steamed liquor with the *S. cerevisiae* strain M 2016785 to produce a second liquor,
    steaming the second liquor to produce a steamed second liquor, and
    blending the steamed first liquor and the steamed second liquor to produce Baijiu,
    wherein the Baijiu has a β-phenylethanol content of at least 100 mg/L.

8. The fermented food of claim 3, wherein the alcohol is fruit wine, and wherein adding the fermented *S. cerevisiae* strain M 2016785 starter culture to food further comprises:
    adding the fermented *S. cerevisiae* strain M 2016785 starter culture to sugar and one or more of: mulberry juice, hawthorn wine, bayberry juice, and *Aronia* juice, and
    fermenting the sugar, *S. cerevisiae* strain M 2016785, and juice under conditions that produce β-phenylethanol, and
    wherein the fruit wine has a β-phenylethanol content of at least 350 mg/L.

9. The fermented food of claim 8, wherein the fruit wine is obtained according to following steps:
(a) cleaning fruit raw materials, crushing, pressing, and separating to obtain a juice;
(b) adding white granulated sugar to the juice with stirring;
(c) adding 160 mg/L of potassium pyrosulfite, 100 mg/L of pectinase into a fermentation tank with stirring;
(d) activating a seed solution of the *S. cerevisiae* strain M 2016785, culturing in a YPD medium comprising 1% yeast extract, 2% peptone, and 2% glucose for 12 h or longer; or adding 2% lyophilized powder of the *S. cerevisiae* strain M 2016785 and stirring for 30 to 60 min at 38° C.;
(e) inoculating the activated seed solution or bacterial solution of lyophilized powder in the previous step into the fermentation tank for pre-fermentation; after inoculation, controlling the temperature at 23 to 25° C., starting the fermentation after 12 to 24 h, and controlling the temperature at 20 to 23° C. after starting the fermentation;
(f) after the pre-fermentation, separating the yeast in the fermentation broth, and adding sulfur dioxide;
(g) maintaining the temperature to be below 20° C., adding a clarifying agent, fully mixing, and fermenting for 16 to 24 days; and
(h) filtering and draining liquor at a bottom of the fermentation tank and filtering an upper liquid.

10. The fermented food of claim 2, wherein the soy sauce is obtained according to following steps:
mixing and steaming soybean meal and wheat,
inoculating *Aspergillus oryzae*,
adding salt water to make a soy sauce mash having a salt content of 18% and water content of 65%,
stirring and mixing well,
inoculating the *S. cerevisiae* strain M 2016785 into the steamed and cooled soybean meal and wheat,
adding fresh water,
culturing to produce a seeding yeast M 2016785 to be added to a soy sauce mash,
inoculating the seeding yeast M 2016785 when the temperature of the soy sauce mash is increased to 20° C. during the fermentation process,
fermenting for 5 months, and
pressing, filtering, and clarifying the soy sauce mash to obtain the soy sauce, and
wherein the soy sauce has a β-phenylethanol content of at least 200 mg/L.

11. The fermented food of claim 2, wherein the soy sauce is obtained according to following steps:
mixing and steaming soybean meal and wheat,
inoculating *Aspergillus oryzae*,
adding salt water to make a soy sauce mash having a salt content of 7% and a water content of 40%,
stirring and mixing well,
inoculating the *S. cerevisiae* strain M 2016785 into part of the steamed and cooled soybean meal and wheat,
adding fresh water,
culturing to produce a seeding yeast M 2016785,
inoculating the seeding yeast M 2016785 into the soy sauce mash fermentation system,
controlling the product temperature at 40° C.,
fermenting for 15 days,
removing impurities and precipitates from the soy sauce mash, and
filtering and clarifying the resulted soy sauce mash to obtain the soy sauce, and
wherein the soy sauce has a β-phenylethanol content of at least 200 mg/L.

12. The fermented food of claim 1, wherein the liquid culture comprises no added phenylalanine precursor.

13. The fermented food of claim 1, wherein the *S. cerevisiae* strain M 2016785 produces twice as much β-phenylethanol in the fermenting step as compared to wild type yeast fermented under similar conditions.

14. The fermented food of claim 13, wherein the liquid culture comprises no added phenylalanine precursor.

* * * * *